(12) United States Patent
Lundberg et al.

(10) Patent No.: US 11,372,093 B2
(45) Date of Patent: Jun. 28, 2022

(54) AUTOMATED FAULT DETECTION AND CORRECTION IN AN ULTRASOUND IMAGING SYSTEM

(71) Applicant: FUJIFILM SonoSite, Inc., Bothell, WA (US)

(72) Inventors: Andrew Lundberg, Woodinville, WA (US); John Kook, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 664 days.

(21) Appl. No.: 16/132,262

(22) Filed: Sep. 14, 2018

(65) Prior Publication Data

US 2020/0088862 A1 Mar. 19, 2020

(51) Int. Cl.
| | |
|---|---|
| G03B 42/06 | (2021.01) |
| G01S 7/52 | (2006.01) |
| G06N 3/08 | (2006.01) |
| G01S 15/89 | (2006.01) |
| G06N 3/04 | (2006.01) |

(52) U.S. Cl.
CPC ........ G01S 7/5205 (2013.01); G01S 7/52053 (2013.01); G01S 15/8911 (2013.01); G06N 3/04 (2013.01); G06N 3/08 (2013.01)

(58) Field of Classification Search
None
See application file for complete search history.

(56) References Cited

U.S. PATENT DOCUMENTS

| | | | | |
|---|---|---|---|---|
| 3,801,978 A | * | 4/1974 | Gershberg | G08B 13/2494 340/516 |
| 4,743,886 A | * | 5/1988 | Steiner | G01S 7/52004 340/514 |
| 4,757,258 A | * | 7/1988 | Kelly, Jr. | F22B 37/003 165/11.2 |
| 4,791,915 A | * | 12/1988 | Barsotti | A61H 23/0245 601/2 |

(Continued)

FOREIGN PATENT DOCUMENTS

KR 1020110132606 12/2011

OTHER PUBLICATIONS

Jäger, Georg, et al. "Assessing neural networks for sensor fault detection." 2014 IEEE international conference on computational intelligence and virtual environments for measurement systems and applications (CIVEMSA). IEEE, 2014. (Year: 2014).*

(Continued)

*Primary Examiner* — Isam A Alsomiri
*Assistant Examiner* — Jonathan D Armstrong
(74) *Attorney, Agent, or Firm* — Womble Bond Dickinson (US) LLP

(57) ABSTRACT

A processor in an ultrasound imaging system identifies faults or errors in the system. In one embodiment, fault or error conditions are detected by monitoring system parameters during a self-test. In another embodiment, a processor provides ultrasound image data to a trained neural network to identify fault conditions in a transducer or the imaging system. In some embodiments, the processor makes adjustments to one or more operating parameters to compensate for the identified fault conditions so that the system continues to operate and produce images with the detected fault condition.

20 Claims, 5 Drawing Sheets

(56) References Cited

U.S. PATENT DOCUMENTS

| | | | | |
|---|---|---|---|---|
| 4,831,565 | A * | 5/1989 | Woodward | G01F 23/2962 367/99 |
| 4,868,445 | A * | 9/1989 | Wand | B06B 1/0253 310/316.01 |
| 5,347,273 | A * | 9/1994 | Katiraie | A61H 3/061 340/435 |
| 5,483,501 | A * | 1/1996 | Park | B06B 1/0688 367/140 |
| 5,517,994 | A * | 5/1996 | Burke | B06B 1/0622 600/437 |
| 5,808,177 | A * | 9/1998 | Bonnefoy | G01H 3/005 73/1.82 |
| 5,883,573 | A * | 3/1999 | Mazeiko, Jr. | G08B 29/10 340/506 |
| 6,040,765 | A * | 3/2000 | Cherry | B60Q 1/48 180/167 |
| 6,270,460 | B1 * | 8/2001 | McCartan | A61B 8/12 600/459 |
| 6,497,660 | B1 * | 12/2002 | Dillman | G01S 7/52025 600/437 |
| 2003/0135244 | A1 | 7/2003 | Esler | |
| 2003/0164658 | A1 * | 9/2003 | Saraf | B06B 1/0261 310/317 |
| 2004/0004905 | A1 * | 1/2004 | Lyon | G01S 7/52004 367/13 |
| 2004/0090316 | A1 * | 5/2004 | Li | G01S 15/931 340/435 |
| 2005/0061848 | A1 * | 3/2005 | Johansen | B29C 65/08 228/1.1 |
| 2005/0124899 | A1 * | 6/2005 | Byrd | A61B 8/12 600/467 |
| 2006/0011707 | A1 * | 1/2006 | Johansen | B29C 66/92921 228/110.1 |
| 2006/0213952 | A1 * | 9/2006 | Johansen | B29C 66/96 228/1.1 |
| 2010/0204766 | A1 * | 8/2010 | Zdeblick | A61N 1/056 607/119 |
| 2011/0083708 | A1 * | 4/2011 | Puskas | B08B 3/12 134/58 R |
| 2012/0316796 | A1 | 12/2012 | Goodman et al. | |
| 2014/0184383 | A1 * | 7/2014 | Wodnicki | H04N 5/367 340/4.3 |
| 2017/0160329 | A1 * | 6/2017 | Jeon | G01R 31/52 |
| 2017/0269039 | A1 * | 9/2017 | Bagge | G01N 29/24 |
| 2018/0274921 | A1 * | 9/2018 | Matsukawa | G01C 19/5607 |
| 2018/0279995 | A1 * | 10/2018 | Doyle | A61B 8/06 |
| 2020/0166640 | A1 * | 5/2020 | Schmidt | G01S 7/524 |
| 2020/0233071 | A1 * | 7/2020 | Hustava | G01S 7/52004 |
| 2020/0329324 | A1 * | 10/2020 | Loeppert | H04R 19/04 |

OTHER PUBLICATIONS

Jaradat, Mohammad Abdel Kareem, and Reza Langari. "A hybrid intelligent system for fault detection and sensor fusion." Applied Soft Computing 9.1 (2009): 415-422. (Year: 2009).*

International Search Report and Written Opinion for Application No. PCT/US2019/050669, dated Jan. 13, 2020, 11 pages.

Shaun W. Lawson et al., "Automatic detection of defects in industrial ultrasound images using a neural network," Proceedings of SPIE—The International Society for Optical Engineering [online].

Issam Oaffou et al., "A reinforcement learning method to adjust parameter of a texture segmentation," 2010 The 7th International Conference on Informatics and Systems (INFOS) [online].

International Preliminary Report and Written Opinion on the Patentability of Application No. PCT/US2019/050669 dated Mar. 25, 2021, 7 pages.

* cited by examiner

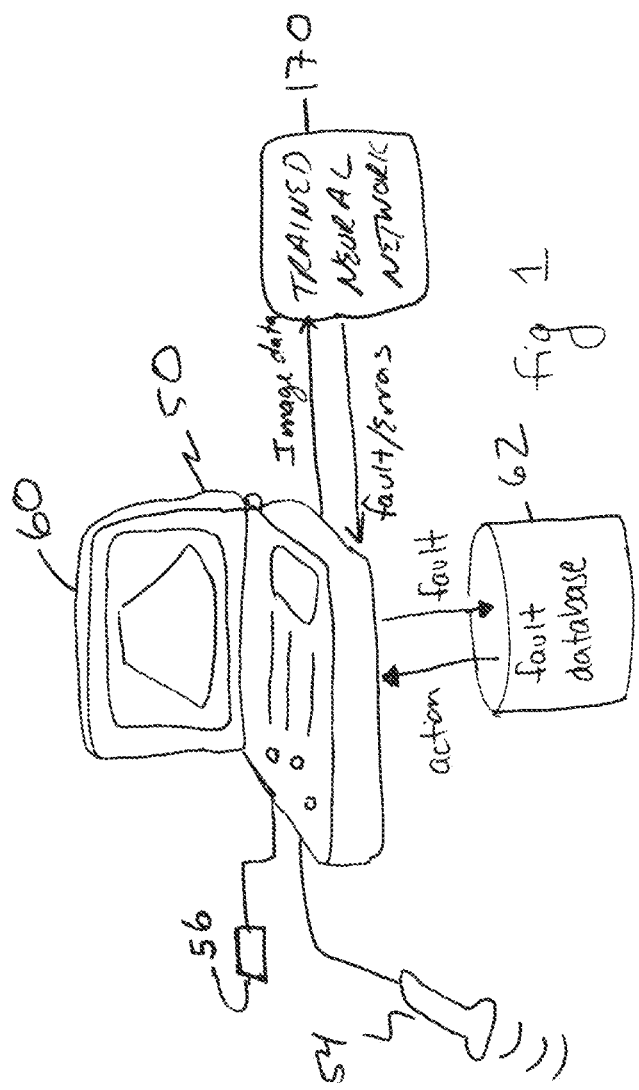

AUTOMATED FAULT DETECTION AND CORRECTION IN AN ULTRASOUND IMAGING SYSTEM

TECHNICAL FIELD

The disclosed technology relates to ultrasound imaging systems and in particular to ultrasound systems that can detect and adjust for system faults.

BACKGROUND

Due to its ease of use and non-ionizing radiation, ultrasound is an increasingly used imaging modality for human and animal subjects. In addition to providing images of internal body tissues, ultrasound is used to provide quantitative assessments of physiological functions by researchers or medical care providers. One common problem with ultrasound systems and ultrasound transducers in particular, is that they are relatively portable and hence easy to abuse. Dropping a transducer or physically damaging the interconnecting cable can cause one or more channels to stop working or to operate erratically. Since the system portion of equipment can be damaged when operated with certain types of transducer faults, some ultrasound imaging systems stop imaging all together if a fault is detected. This can be frustrating in emergency or other situations where users would prefer to have a less than optimal image over having no image if the fault is not the type that will damage the equipment further or potentially injure a subject. In other situations, the system may keep imaging but does not inform the user that the images are not optimal and the user may interpret erroneous ultrasound data as actual data.

SUMMARY

To address the problems described above and others, the disclosed technology is an ultrasound system that detects system faults or errors and takes one or more programmed actions such as: preventing operation of the system; adjusting for a detected fault in order to allow the system to produce images without interruption; and alerting an operator that images were obtained with a detected fault.

In one embodiment, beamforming circuitry for a number of transmit/receive channels is connected to transducer elements through a programmable multiplexer. A processor controls a self-test in which the multiplexer is set to disconnect one or more transducer probes from the beamforming circuitry. A test pulse is generated while the transducer(s) are disconnected. Faults are detected based on the measured current drawn from the power supply with the test pulse. If current is detected, transmit pulsers could be selectively disabled to isolate the channel with a fault. Depending upon the extent of the fault, the processor can compensate thereafter.

In another embodiment, a processor analyzes signals received on the channels when the multiplexer has connected or disconnected the transducer(s). Acoustic echo information received on a channel that is supposedly disconnected indicates that there is likely a system multiplexer fault. In a like manner, acoustic echo information received on a channel of a fully connected transducer is compared to adjacent channels. Abnormal signals indicate faulty elements. Upon detection of a fault, the processor can take programmed action to compensate for the particular fault.

In yet another embodiment, a processor controls a multiplexer to disconnect the transducer from the beamforming circuitry. At the same time, a ground clamp in the multiplexer for each transducer element is set and the bias power supply is enabled and monitored. If excessive current flow is detected, indicating a bias voltage fault within the transducer, the processor could recommend this transducer not be used, but instead be detached and repaired.

In yet another embodiment, a processor in an ultrasound imaging system is programmed to provide ultrasound image data to a neural network that is trained to identify faults or errors in the system from the image data. In one embodiment, the neural network returns a probability of a detected fault or error to the processor. Upon detection of an identified fault or error, the processor is programmed to take one or more actions such as preventing operation of the system; adjusting or compensating for a detected fault in order to allow the system to continue to produce images without damaging the system; and alerting an operator that images were obtained with a detected fault.

BRIEF DESCRIPTION OF THE DRAWINGS

FIG. 1 shows a representative ultrasound system for producing ultrasound images in accordance with an embodiment of the disclosed technology;

DETAILED DESCRIPTION

Figure 2A:
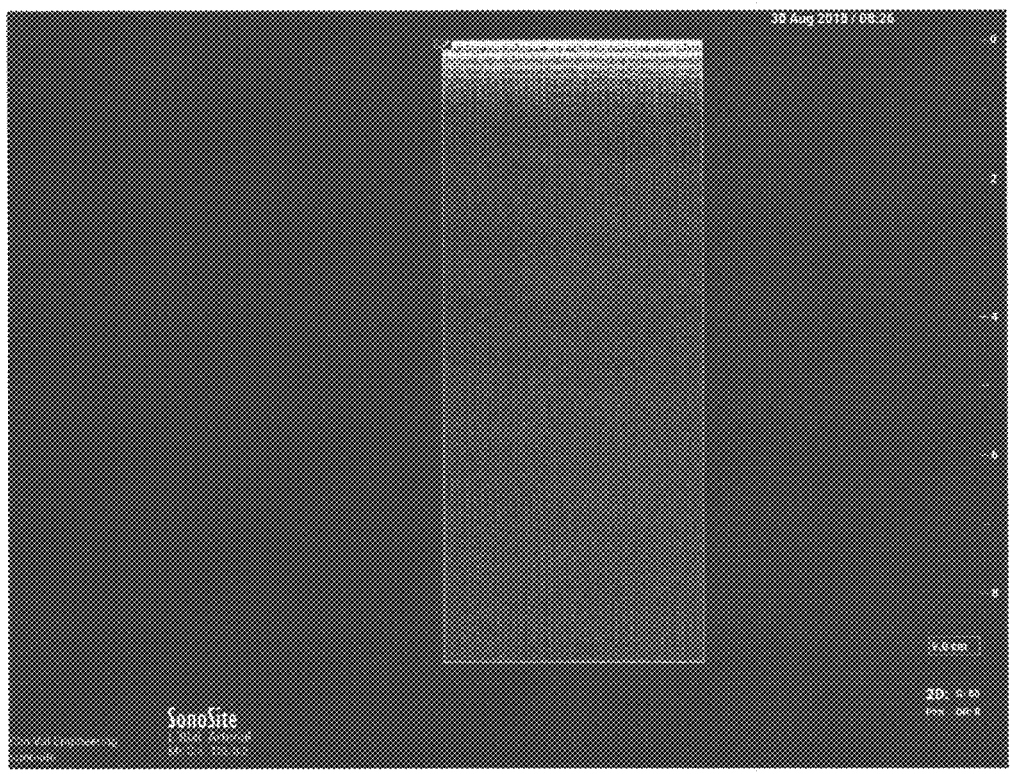
FIG. 2A shows an ultrasound image produced by a normally operating ultrasound imaging system.

As described above, many ultrasound systems perform a diagnostic self-test upon initial power up of the device. If a fault is detected, the systems will often prevent further operation or use of the system until it is inspected and repaired by a certified technician. While this approach can prevent damage to the system and the production of possibly erroneous images, it often frustrates users in emergency situations where any image of the subject may be better than no image.

To overcome these deficiencies, the disclosed technology is directed to a system for automatically detecting faults or error conditions in an ultrasound imaging system. Upon detection of a fault or error, a processor is programmed to take one or more actions. In some embodiments, the processor is programmed to continue to obtain and display ultrasound images if the processor determines that imaging can continue without subjecting the system to further damage. In other embodiments, the processor is programmed to stop operation if a detected fault or error will further damage the system. In other embodiments, the processor is programmed to continue imaging and compensate for a detected fault or error. In still other embodiments, the processor is programmed to continue imaging and alert an operator that the fault or error has been detected.

FIG. 1 shows a representative ultrasound imaging system with which the disclosed technology can be implemented. An ultrasound imaging system 50 can comprise a hand-held, portable or cart-based imaging system. The ultrasound system 50 connects with one or more ultrasound transducers 54 that transmit ultrasound acoustic signals into a subject (not shown) and receive the corresponding acoustic echo signals from the subject. In some embodiments, the ultrasound system 50 can receive signals from one or more additional external sensors 56 such as $SPO_2$ sensors, EKG sensors, respiration sensors or the like. The ultrasound imaging system 50 includes one or more displays on which ultrasound data are displayed. The displays may include a touch sensitive screen such that a user can operate the system with touch commands. In some embodiments, additional controls (track balls, buttons, keys, trackpad, voice activated controls, motion sensors etc.) may also be provided for the user to interact with. The ultrasound imaging system 50 also includes communication circuitry (e.g. modem, NIC, Bluetooth or 802.11 radio etc.) to allow the system to connect to one or more remotely located systems (not shown) through a wired or wireless data communication link.

The ultrasound imaging system 50 includes signal and image processing circuitry having one or more processors (e.g. CPUs, DSPs, GPUs, ASICs, FPGAs or a combination thereof) that are configured to produce image data from returned analog echo signals. As will be explained in detail below, the imaging system is configured to detect faults or errors in the system and determine a correct mode of operation. In one embodiment, a database 62 stores information about a number of different faults or error conditions and what corresponding corrective action should be taken by the processor. The database receives a code, numerical identifier or description of a particular fault or error condition (also referred to as a "fault condition") and returns information about what action the processor should take for the particular fault or error condition provided. In some embodiments, the imaging system performs a self-test by measuring operating conditions within the imaging system to detect a fault or error condition. In other embodiments, the processor executes programmed instructions stored in a processor readable memory or performs pre-determined logical operations to implement a neural network 170 that is trained to analyze ultrasound image data in order to identify faults or error conditions in the imaging system. In the disclosed embodiments, the faults or error conditions can be in the ultrasound imaging system itself, in the transducer 54 or both. Examples of such error conditions or faults include, but are not limited to, shorted or open transducer elements, quantization errors in an A/D converter, errors in the receive amplifiers or filters, beamformer FPGA errors, errors in FPGA transmit circuitry, multiplexers, power amplifiers or the like.

Figure 2B:
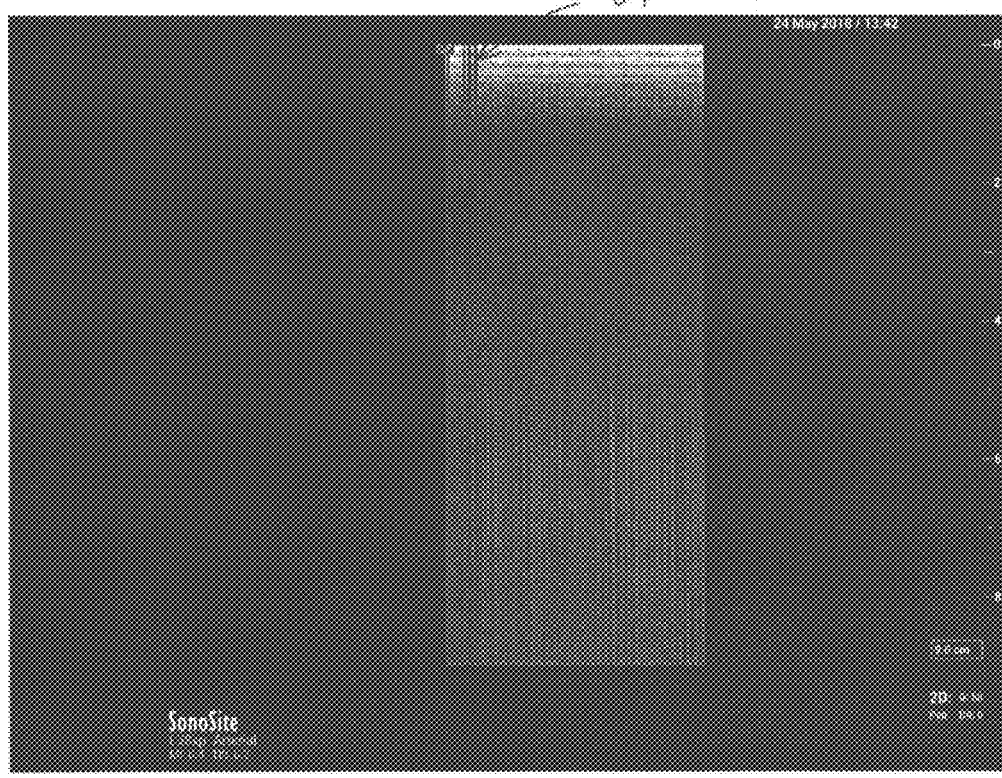
FIG. 2B shows an ultrasound image produced by an ultrasound imaging system with noise issues and failed receive channels.

FIG. 2A shows a representative ultrasound image 80 taken from a fully operation ultrasound imaging system, while FIG. 2B shows an image 82 having noise problems and malfunctioning receive channels. The image 82 has a number of artifacts such as a pattern of dark beam lines 84 corresponding to the malfunctioning receive channels and a pattern of white streaks having increase noise. To a trained ultrasound technician such artifacts suggest where the faults or error conditions in the ultrasound imaging system are occurring. By detecting these types of errors, the processor in the ultrasound system of the disclosed technology can compensate for the artifacts. Such compensation may include filling in the data for an artifact line by utilizing data from neighboring elements (pre-beamforming) or from neighboring beams (post-beamforming) to approximate the compromised data lessening the discontinuity in the beam lines. If the processor determines that the fault causing the artifact may further damage the imaging system, then the processor may disable further imaging until the fault can be repaired.

Figure 3:
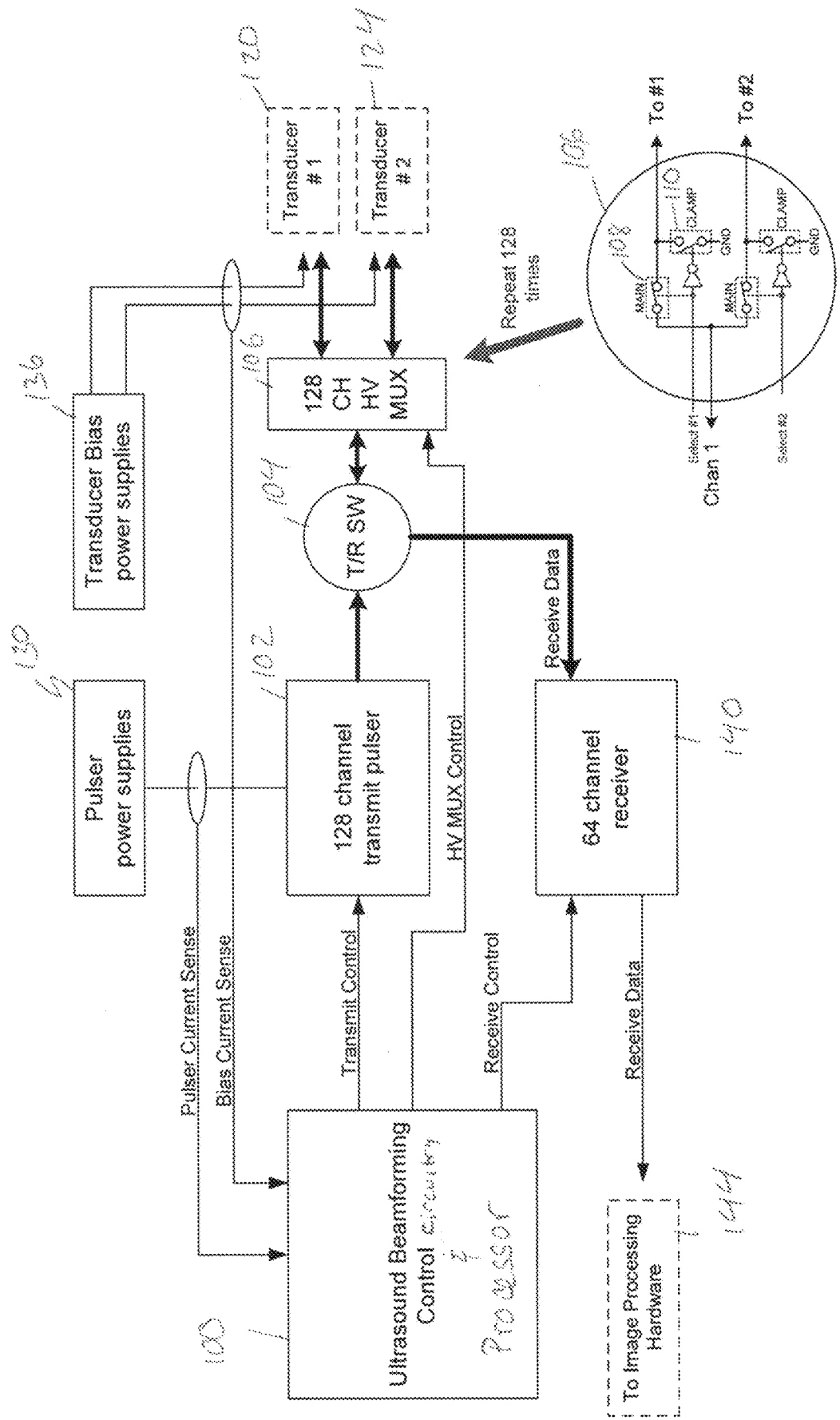
FIG. 3 is a block diagram of beamforming transmit/receive circuitry in an ultrasound imaging system that allows a processor to detect fault/errors in accordance with an embodiment of the disclosed technology.

FIG. 3 is a block diagram of a transmit/receive path in an ultrasound imaging system in accordance with one embodiment of the disclosed technology. The imaging system includes a processor and beamforming control circuitry 100. The processor executes program steps to control the operation of the ultrasound system while the beamforming control circuitry 100 controls the timing and magnitude of the pulses that are provided to the transducer elements to steer a beam in a particular direction or perform a particular type of imaging (e.g. B-mode, M-mode, Doppler etc.) A pulser circuit 102 provides the high voltage pulses to the individual transducer elements through a transmit/receive switch 104 and a multiplexer 106. In one embodiment, the multiplexer can direct the signals to one, two or no transducer elements though switches 108. In one embodiment, the multiplexer (HDL6M06502B) includes a ground clamp 110 for each output of the multiplexer. The ground clamp 110 is open when the corresponding switch 108 is closed and the ground clamp is closed when the corresponding switch 108 is open. In the embodiment shown, the multiplexer 106 is coupled to a pair of transducer 120, 124 each having a number of individual transducer elements.

Power for the pulser 102 is provided by a pulser power supply 130. A transducer bias supply 136 provides the voltage rails for the transducers 120, 124. A receiver 140 (e.g. low noise amplifiers, A/D converters etc.) is connected to the transmit/receive switch 104. During transmit, the transmit/receive switch 104 connects the multiplexer 106 to the pulser 102. During receive, the transmit/receive switch connects the receiver 140 to the multiplexer 106. The output of the receiver 140 feeds imaging processing hardware 144.

To test for faults or errors in the transmit/receive path, the processor 100 is programmed to set the switches 108 in the multiplexer in the open position so that the pulser 102 is disconnected from the transducers 120, 124 and the ground clamps 110 are set. In this configuration, all the transducer elements are disconnected from the pulser. The processor provides a test pulse to the transducer elements. The processor 100 receives a signal from a current sensor that senses the current provided by the pulser power supply 130. If all the transducer elements are disconnected, the current should be minimal. If, due to a fault of some sort, a switch 108 in the multiplexer is in a closed position, the current draw will exceed some threshold minimum and can be detected. In this case, the processor is subsequently programmed to apply test pulses to individual channels in order to determine which one(s) are associated with the increased current draw. Upon determining the extent of the fault, the processor is programmed to take steps to lessen the effect of the fault. In one example, the processor 100 is programmed to prevent signals from being transmitted on the faulty channel and to average the data that should be received on the faulty channel with the data signals received by neighboring elements.

In some embodiments, the multiplexer 106 may lack the ground clamps 110. In this embodiment, the processor 100 is programmed to analyze signals on each channel when the multiplexer for the channel is set to "open." If a signal other than noise is received, the processor determines that there is a fault in the multiplexer switch or somewhere else in the receive channel. The processor is then programmed to compensate for the fault by, for example, not transmitting on that channel and filling in data for the faulty channel with data from neighboring channels.

In another embodiment, the processor monitors the bias currents supplied by the bias supply 136 when a transducer 120, 124 is connected to the system. With the switches 108 in the multiplexer 106 open and the ground clamps 110 closed, the transducer should be disconnected from the beamforming circuitry of the ultrasound system. If an abnormal current spike occurs when the transducer bias power supply is energized, the processor determines that there is a fault in the transducer. By monitoring the current provided by the bias power supply 136, shorts can be detected without passing current through the transmit/receive switch 104 and possibly damaging it.

As discussed above, in some embodiments, a processor is programmed to use a trained neural network to detect faults/errors. Certain faults or error conditions may produce artifacts in the corresponding ultrasound images that are detectable by the trained neural network 170. After the neural network 170 is trained, a processor provides image data produced by the imaging processing electronics to the neural network and the neural network returns a probability (percentage) that image data were obtained with an imaging system having a known fault or error condition. For example, a transducer with an inoperative element may be associated with images having a dark region along a beam line in an image. A bad receive channel may produce dark lines or regions in an image as shown in FIG. 2B. In some embodiments, the neural network 170 analyzes the image data and returns a probability or percentage like 0.96 and an associated error identifier such as "#4—transducer element 38 non-functioning" that are read by the processor to diagnose the fault/error condition.

In one embodiment, the database 62 (FIG. 1) stores records of known faults and error conditions and one or more actions to be taken to compensate for the fault/error condition or if imaging can continue. Upon identification of a fault or error condition, a processor is programmed to use the database 62 to determine the response to the detected fault/error condition.

Upon receipt of the results from the neural network, the processor is programmed to compensate or adjust one or more parameters to correct for the fault. For example, transducer elements that are non-functional can be compensated for by increasing the contribution from the signals from neighboring elements. Faulty amplifiers or errors in other signal processing components can be compensated by not processing the data from a bad TX or RX channel or by adjusting the ultrasound data that is received to bring the data in line with the data that would be received by a fully functional component prior to combining the data with the data from the other channels and producing an image. In other embodiments, the processor provides a list of options for the user to select how the system should respond to a detected fault/error. Such a list may include a warning that continued operation with the detected fault may harm the imaging system or the transducer and void any warranty protection etc. In other embodiments, the user may be given a choice of how they would like to adjust or replace the data for a faulty channel (averaging neighboring beam lines, copying data for a faulty receive channel etc.). In some embodiments, the data for a channel having a detected fault may be color coded or otherwise marked so that an operator can see that the data is synthesized rather than received from tissue. In other embodiments, the adjusted or compensated data is synthesized to blend in seamlessly with the data from the fully functional channels.

Figure 4:
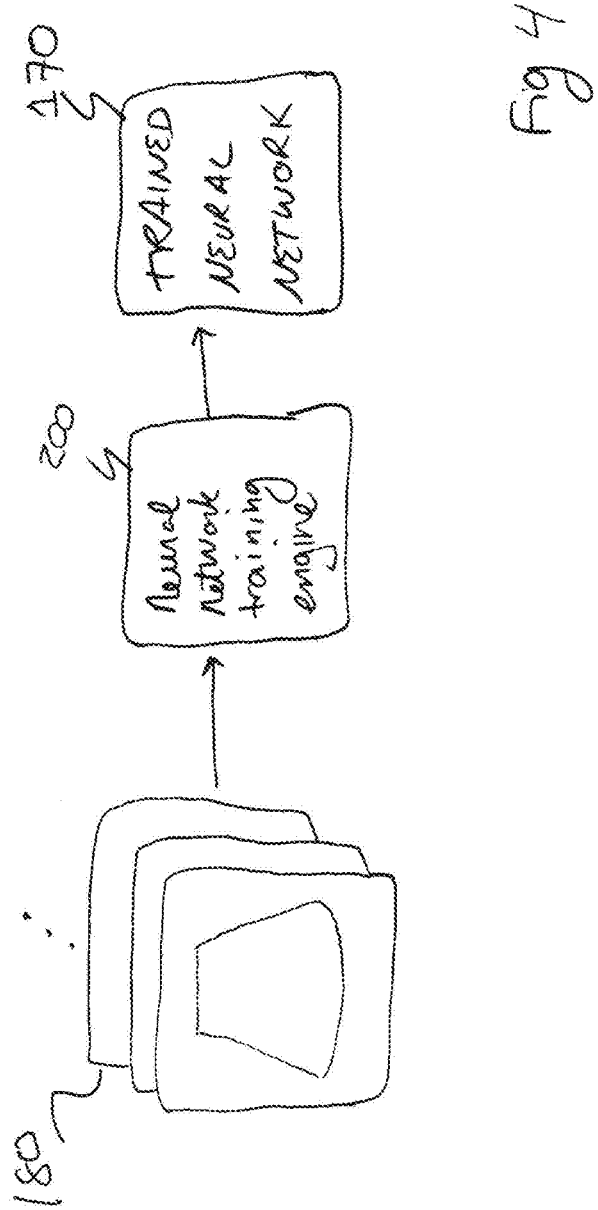
FIG. 4 shows how a neural network is trained with a number of test images in accordance with an embodiment of the disclosed technology.

To train the neural network 170, a number of test images 180 are provided to a neural network training engine 200 as shown in FIG. 4. The test images 180 are images or portions of images obtained with an imaging system or transducer with known fault(s). In one embodiment, the image data are a uniform size such as 256 pixels wide by 128 pixels high with each pixel having an eight-bit black and white brightness value. Other image sizes can also be used such as 256 pixels wide by 256 pixels high or 512 pixels wide by 64 pixels high etc. As used herein, the term "image" is intended to broadly mean a representation of ultrasound echo data. The image may include post scan converted data, pre-scan converted data or raw RF data. In addition, not all the data for an image may be used. In addition, the system can be configured to better isolate errors in the image data, through methods like channel isolation (transmitting and/or receiving only on one element), depth dependent frequency filtering, controlling beam firing order and system and transducer multiplexer selection. A portion or section of the data of a known size may be used to train the neural network.

As will be appreciated by those skilled in the art of machine learning, neural networks and artificial intelligence, a large number (e.g. 1,000-14,000 or more) of training images are supplied to the neural network training engine 200 to allow the engine to determine a number of filter weights and bias values so that a convolutional neural network using the weights and bias value will return a probability that the image was obtained with an ultrasound imaging system or transducer having a particular fault or error condition. To one skilled in the art, it is also understandable that the total number of training images can be increased using data augmentation whereby an initial base set of images are increased though linear and nonlinear modifications thereby producing additional training data. For example, augmentation may include both linear and nonlinear scaling or brightness or contrast changes.

In one embodiment, the training data images are collected and categorized by ultrasound repair technicians diagnosing faults or other error conditions from imaging systems or transducers that are returned for repair or from errors discovered during the manufacturing process. Images are categorized and stored in a database along with meta data or a description of a fault or error condition. The image data are cropped or otherwise edited to conform to a standard dimension to be used to train the neural network.

For one skilled it the art, it can be understood that a number of different machine learning models can be employed. For example, variants of freely available models can be used such as VGG5, VGG16 (Visual Geometry Group at Oxford), and Mobile Net (Google). Custom models can also be developed. Tradeoffs using different models can include prediction accuracy and size which will affect inference speed on embedded devices.

A Python framework using Keras and Tensorflow can be used to train a model using the prepared and augmented data. An Adam optimizer with variable learning rate can be employed over approximately 1 million training examples. Other optimizers can be used; for example SGD (Stochastic gradient descent). The tradeoffs using different optimizers include convergence time, and training speed. A combination of two or more different optimizers can also be used.

Neural network models themselves are generally interchangeable, with some providing advantages over others. For example, computational complexity and output accuracy are considerations. Modifications could include using a different model, changing the number of layers, or adding additional layers such as dense layers or addition convolutional layers Once the model is trained, the accuracy can be tested using image data obtained with a system/transducer having an identified fault. The neural network 170 should identify the fault based on changes in the ultrasound image data versus image data from a normally operating transducer/ultrasound system.

During use, the trained neural network 170 is configured to receive input image data of the same size with which the neural network was trained (e.g. 256×128×1) and to produce an output data indicating the probability of the image having been obtained with an imaging system or transducer having a particular fault or error condition. In one embodiment, the output from the neural network (return values from the trained neural network) is a list of faults or error conditions that the neural network 170 has been trained to detect and a probability or likelihood that an input image was captured by a transducer or imaging system having a particular fault/error condition. For example, in one embodiment, the system is trained to detect 200 known faults or error conditions. The neural network 170 therefore returns a 200 element array or a list with the probability (e.g. percentage) that an image is obtained with a transducer or imaging system having one or more of the known 200 faults/error conditions.

A processor in the imaging system receives the array and scans the list probabilities that are above a threshold. For example, an entry [4, 0.78] indicates that there is a 78% chance that an image was obtained from an imaging transducer having defined error condition #4 (e.g. transducer element 38 is an open circuit) or [16, 0.86] e.g. 86% chance that error condition #16 (multiplexer switch shorted) has occurred. It is possible that two or more error conditions/faults may be identified in the list. In some embodiments, the probabilities identified by the neural network all sum to 1.0. One entry in the return data may indicate that the transducer/imaging system are operating normally.

In some embodiments, the processor of the imaging system provides image data to the trained neural network 170 upon an initial power on self-test. Corrections or adjustments to imaging parameters can be made before a scan procedure begins. In other embodiments, a processor provides image data to the trained neural network 170 during a scan procedure and corrections or adjustments to imaging parameters are made during the scan. For example, the neural network 170 is provided with images (or portions of images) as a scan is occurring and the neural network 170 identifies possible faults or error conditions as the system is being used. If the neural network examines the images and determines that there is a problem with an amplifier in a receive channel for example, then the processor may compensate for the gain of the amplifier to correct for the error.

As indicated above, once the neural network 170 has been trained, the processor receives the output of the network and adjusts one or more operating parameters to compensate for the detected faults or error conditions. The processor may adjust the gain of signals received on a faulty channel, may not transmit from a transducer element that is found to be defective, can average signals received from elements neighboring a faulty element etc. In some cases, the processor adjusts parameters that are internal to the imaging system (gain of amplifiers, averaging data for a bad channel, copying data for a bad channel, omitting transmissions on a particular transducer element etc.). In other cases, the processor may prompt the user to make an adjustment to their examination procedure such as instructing the user to apply more ultrasound gel, manually adjust the gain etc. In other embodiments, the user is alerted to a detected fault/error condition and is prompted to determine if the user wants to continue performing an examination with the detected fault/error condition. Such a prompt may include a warning about damaging the transducer or imaging system by continued use or may provide a prognosis that continued use may cause another error or fault to occur. In this case, the user can decide for themselves if they want to take the risks associated with continued operation of the system.

Figure 5:
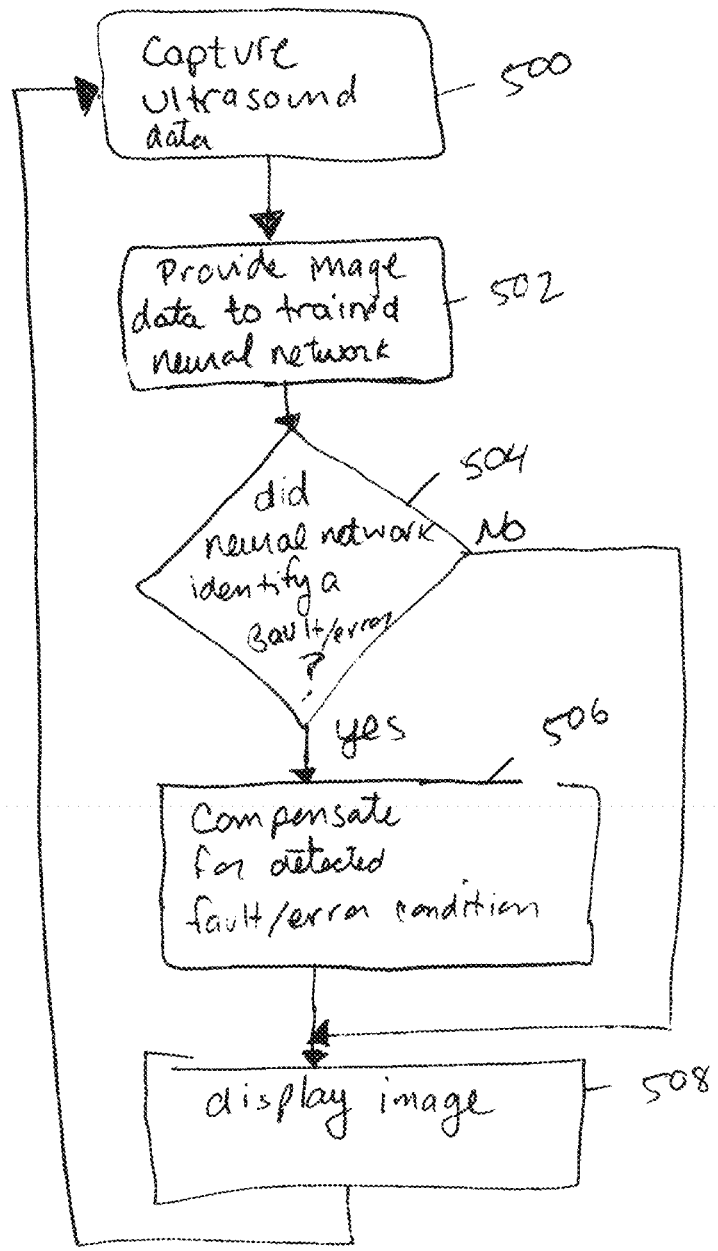
FIG. 5 is a logic diagram of steps taken by a programmed processor to use a trained neural network to detect faults or errors in an ultrasound imaging system and to compensate for such detected faults or errors in accordance with an embodiment of the disclosed technology.

FIG. 5 is a flowchart of logic performed by a programmed processor in an ultrasound system in accordance with one embodiment of the disclosed technology. Beginning at 500, the processor captures ultrasound image data from a connected transducer. Image data of the same size that was used to train the neural network is provided to the neural network at 502 to see if the neural network can detect one or more faults or error conditions. At 504, the processor analyzes the results from the neural network indicating whether the image was obtained using a transducer or imaging system having a particular fault or error condition. If an error or fault is detected, the processor adjusts one or more operating parameters (or prompts a user to make the adjustments) to compensate for the detected fault or error condition at 506 and displays the image with the compensation at 508. If no fault or error is detected at 506, then the image data are displayed at 508 without making any adjustments.

As indicated, because the processor is programmed to detect faults and to make adjustments to compensate for the detected faults/errors, the imaging system can continue to produce images even though it has a detected fault or error. This is a benefit for first responders, emergency room physicians, soldiers and other individuals who need an imaging system that can continue to operate the system even if it is out of the manufacturer's specifications.

In one embodiment, images produced with a detected fault/error condition are stored with a record of the compensation that was applied to the ultrasound data to correct for the fault. In some instances, the viewer can view an image with and without the correction and can select which image they prefer. Once the selection is determined, additional images can be obtained with or without supplying each image to the neural network. In some embodiments, the compensation applied for a detected fault or error condition may not be optimal but may be user preferred. In some embodiments, the database 62 that stores corrections or adjustments for a detected fault or error can store a record of a user-preferred change instead of a pre-defined correction or adjustment. In some embodiments, the database 62 stores a record of system operation after a fault or error has been detected and a change made to an operating parameter so that the system can record whether the change that was made was effective in compensating for the detected fault or error condition. In some embodiments, databases from multiple imaging systems can be combined and updated reflecting the changes most often selected by users or with updated changes or parameters that are found to better compensate for an error. In some embodiments the database 62 is stored locally on the imaging system. If a communication link exists between the imaging system and a remote computer (server), the database 62 may be hosted remotely and the processor of the imaging system programmed to query the remote database for a correction or an adjustment to be applied for a detected fault/error.

Embodiments of the subject matter and the operations described in this specification can be implemented in digital electronic circuitry, or in software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., EEPROM, flash memory, CD-ROM, magnetic disks, or other storage devices). The operations described in this specification can be implemented as operations performed by a data processing apparatus on instructions stored on one or more computer-readable storage devices or received from other sources.

The term "processor" encompasses all kinds of apparatus, devices, and machines for processing data, including by way of example a programmable processor, microcontroller, digital signal processor (DSP), graphics processor (GPU), a computer, a system on a chip, or multiple ones, or combinations, of the foregoing. The apparatus can include special purpose logic circuitry, e.g., an FPGA (field programmable gate array) or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one processor or on multiple processors within the ultrasound imaging system.

Processors suitable for the execution of a computer program include, by way of example, both general and special purpose microprocessors. Generally, a processor will receive instructions and data from a read-only memory or a random access memory or both. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on an ultrasound imaging system having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the system. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. An ultrasound imaging system, comprising:
   a transducer configured to supply ultrasound signals to a subject and to receive ultrasound echo signals from the subject;
   a processor coupled to the transducer;
   a database coupled to the processor to store fault conditions and corresponding actions taken by the processor of the ultrasound imaging system to compensate for the fault conditions;
   wherein the processor is configured to:
      produce ultrasound image data from the ultrasound echo signals;
      supply the ultrasound image data to a neural network
      detect a fault condition in at least the transducer or the ultrasound imaging system based on the ultrasound image data;
      receive an identifier of the fault condition from the neural network;
      identify, from the actions stored in the database, an action to be taken on the identifier of the fault condition;
      adjust one or more operating parameters of the ultrasound imaging system to form one or more adjusted operating parameters by performing the action that has been identified from the actions stored in the database; and
      compensate for the fault condition using the one or more adjusted operating parameters; and
   a display configured to display an ultrasound image obtained with the one or more adjusted operating parameters.

2. The ultrasound imaging system of claim 1, wherein the processor is configured to supply the ultrasound image data to the neural network during a self-test mode or during an examination, and wherein the compensate for the detected fault condition using the one or more adjusted operating parameters is performed to continue to produce ultrasound images without interruption when the fault condition is detected.

3. The ultrasound imaging system of claim 1, wherein the actions include preventing operation of the ultrasound imaging system, adjusting the one or more operating parameters of the ultrasound imaging system for the fault condition for the ultrasound imaging system to produce images without interruption and alerting a user to make one or more changes to an operating parameter to compensate for the fault condition.

4. The ultrasound imaging system of claim 1, wherein the database is configured to store the ultrasound image data along with the fault conditions and the corresponding actions.

5. The ultrasound imaging system of claim 1, wherein the display is configured to further display an additional ultrasound image obtained using the one or more operating parameters.

6. The ultrasound imaging system of claim 1, wherein the database stores a record of a system status detected after the action is performed to adjust the one or more operating parameters after the detected fault condition.

7. The ultrasound imaging system of claim 1, wherein the database stores a record of a change made by a user to an operating parameter to compensate for the detected fault condition.

8. The ultrasound imaging system of claim 1, wherein the processor is configured to provide at least one of a list of one or more actions to be taken in response to the detected fault condition or a prompt for an indication if imaging should continue with the detected fault condition.

9. An ultrasound imaging system, comprising:
a transducer configured to supply ultrasound signals to a subject and to receive ultrasound echo signals from the subject;
a multiplexer that is configured to selectively connect the transducer to a transmit/receive circuitry in the imaging system;
a power supply that supplies power to the transmit/receive circuitry;
a processor configured to:
set the multiplexer into an open position to disconnect the transducer from the transmit/receive circuitry;
deliver a test pulse to the transducer after the multiplexer is set into the open position;
monitor a current drawn from the power supply with the multiplexer in the open position during the test pulse;
detect a fault condition of one or more fault conditions in the transducer or the imaging system, when the current drawn from the power supply exceeds a threshold while the multiplexer is in the open position;
and
adjust one or more operating parameters to form one or more adjusted operating parameters to compensate for the fault condition; and
a display configured to display an ultrasound image obtained using the one or more adjusted operating parameters.

10. The ultrasound imaging system of claim 9, wherein the processor is configured to alert a user to make one or more changes to an operating parameter in response to the fault condition.

11. The ultrasound imaging system of claim 9, wherein the processor is configured to store ultrasound image data along with an indication of a change made to an operating parameter to compensate for the fault condition.

12. The ultrasound imaging system of claim 9, further comprising a database accessible by the processor to store fault conditions and corresponding actions made to change operating parameters to compensate for the fault conditions, and wherein the processor is further configured to identify, from the actions stored in the database, an action to the one or more operating parameters of the ultrasound imaging system based on the fault condition; and wherein the adjust the one or more operating parameter to compensate for the fault condition is by performing the action that has been identified from the database.

13. The ultrasound imaging system of claim 9, wherein the display is further configured to display an additional ultrasound image obtained using the one or more operating parameters.

14. The ultrasound imaging system of claim 9, wherein the processor is configured to prompt a user if imaging should continue with the fault condition.

15. An ultrasound imaging system, comprising:
a transducer having a number of transducer elements configured to supply ultrasound to a subject and to receive ultrasound echo signals from the subject;
a multiplexer with switches that are configured to selectively connect the transducer to a transmit/receive circuitry in the imaging system and a number of ground clamps that ground a transducer element when a switch to the transducer element is open;
a bias power supply that supplies a bias power to the transducer;
a processor configured to:
set the switch of the multiplexer into an open position to disconnect the transducer from the transmit/receive
circuitry in the imaging system;
monitor a current drawn from the bias power supply when
the bias power supply is energized and the switch of the multiplexer is in the open position;
detect a fault condition of one or more fault conditions in the transducer, when the current drawn from the bias power supply exceeds a threshold while the switch of the multiplexer is in the open position and a ground clamp of the number of ground clamps is in a closed position to connect the transducer to the ground; and adjust one or more operating parameters to compensate for the fault condition; and
a display configured to display an ultrasound image obtained with the one or more adjusted parameters.

16. The ultrasound imaging system of claim 15, wherein the processor is configured to alert a user to make one or more changes to an operating parameter to compensate for the fault condition.

17. The ultrasound imaging system of claim 15, wherein the processor is configured to store ultrasound image data along with an indication of a change made to an operating parameter to compensate for the fault condition.

18. The ultrasound imaging system of claim 15, further comprising a database accessible by the processor that stores fault conditions and corresponding actions made to change operating parameters to compensate for the fault conditions, and wherein the processor is further configured to identify, from the actions stored in the database, an action to change the one or more operating parameters of the ultrasound imaging system based on the fault condition; and wherein the adjust the one or more operating parameter to compensate for the fault condition is by performing the action that has been identified from the database.

19. The ultrasound imaging system of claim 15, wherein the display is further is configured to display an additional ultrasound image obtained using the one or more operating parameters.

20. The ultrasound imaging system of claim 15, wherein the processor is configured to prompt a user if imaging should continue with the fault condition.

* * * * *